US00PP35205P2

(12) United States Plant Patent
Whitehouse et al.

(10) Patent No.: US PP35,205 P2
(45) Date of Patent: Jun. 6, 2023

(54) ***FRAGARIA* PLANT NAMED 'MALLING ACE'**

(50) Latin Name: ***Fragaria* x *ananassa***
Varietal Denomination: Malling Ace

(71) Applicant: NIAB, Cambridge (GB)

(72) Inventors: Adam Barrie Whitehouse, Kent (GB); David William Simpson, Taunton (GB); Abigail Johnson, Kent (GB)

(73) Assignee: NIAB, Cambridge (GB)

( * ) Notice: Subject to any disclaimer, the term of this patent is extended or adjusted under 35 U.S.C. 154(b) by 0 days.

(21) Appl. No.: 17/979,152

(22) Filed: Nov. 2, 2022

Related U.S. Application Data

(60) Provisional application No. 63/276,337, filed on Nov. 5, 2021.

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./208, 209
See application file for complete search history.

(56) References Cited

PUBLICATIONS https://www.niab.com/malling-fruits/strawberries/malling-ace. Retrieved from the Internet on Dec. 15, 2022 (3 pages total).*

* cited by examiner

*Primary Examiner* — Susan McCormick Ewoldt
(74) *Attorney, Agent, or Firm* — Penny J. Aguirre

(57) ABSTRACT

A new cultivar of *Fragaria* plant named 'Malling Ace' that is characterized by its semi-upright growth habit, its large leaf size, its attitude of petiole hairs that are slightly outwards, its large sized flowers, its calyx and corolla that are the same size, its flower petals that are white in color, its berries that are slightly longer in relation to width, large in size, conical in shape and medium red in color, flesh that is red in color with a white core and achenes that are positioned below the surface, its sepals that are held outward, its calyx diameter that is slightly larger in relation to the fruit size, its medium to late flowering time and fruit ripening time, and its fully remontant fruit bearing habit.

2 Drawing Sheets

Botanical classification:
*Fragaria* x *ananassa.*
Variety denomination: 'Malling Ace'.

CROSS REFERENCE TO A RELATED APPLICATIONS

This application is also related to a European plant breeders' rights application filed on Oct. 20, 2021, application No. 2020/2580 and a plant breeders' rights application in Morocco on May 26, 2021, application No. 1061/21, and a plant breeders' rights application in Canada on Jul. 7, 2021, application No. 21-10622, and a plant breeders' rights application in Norway on Jun. 3, 2021, application No. 1693, and a plant breeders' rights application in Switzerland on Apr. 22, 2021, application No. 21-3419. The Applicant received the information for the Plant breeders' rights applications directly from the Inventors.

BACKGROUND OF THE INVENTION

The present invention relates to a new and distinct cultivar of *Fragaria*, botanically known as *Fragaria* x *ananassa* and will be referred to hereafter by its cultivar name, 'Malling Ace'. 'Malling Ace' is a day neutral strawberry plant primarily adapted to the climate and growing conditions of the United Kingdom and other regions of similar climate and day length.

The new cultivar was derived from an ongoing breeding program conducted by the Inventors at a farm in Kent, United Kingdom. The objective of the breeding program was to develop a new cultivar of *Fragaria* with high fruit yields, fruit size, and fruit shape. 'Malling Ace' arose from a controlled cross made by the Inventors in February of 2014 between an unpatented selection from the Inventor's breeding program, designated as accession number 'EMR 583' as the female parent and an unpatented selection from the Inventor's breeding program, designated as accession number EMR 556 as the male parent. 'Malling Ace' was selected as a single unique plant in July of 2015 from amongst the seedlings that resulted from the above cross.

Asexual propagation of the new cultivar was first accomplished by rooting stolons in Kent, United Kingdom in July of 2014. Asexual propagation by rooting of stolons and tissue culture using meristematic tissue has shown that the unique characteristics of the new cultivar are stable and reproduced true to type in successive generations.

BRIEF SUMMARY OF THE INVENTION

The following traits have been repeatedly observed and represent the characteristics of the new cultivar. These attributes in combination distinguish 'Malling Ace' as a new and unique cultivar of *Fragaria.*

1. 'Malling Ace' exhibits a semi-upright growth habit.
2. 'Malling Ace' exhibits a large leaf size.

3. 'Malling Ace' exhibits attitude of petiole hairs that are slightly outwards.
4. 'Malling Ace' exhibits large size flowers.
5. 'Malling Ace' exhibits calyx and corolla that are similar in width.
6. 'Malling Ace' exhibits flowers with petals that are white in color.
7. 'Malling Ace' exhibits berries that are slightly longer in relation to width.
8. 'Malling Ace' exhibits berries that are large in size.
9. 'Malling Ace' exhibits berries that are conical in shape.
10. 'Malling Ace' exhibits berries that are medium red in color.
11. 'Malling Ace' exhibits achenes that are positioned below the surface (sunken).
12. 'Malling Ace' exhibits sepals that are held outward.
13. 'Malling Ace' exhibits a calyx diameter that is slightly larger in relation to the fruit diameter.
14. 'Malling Ace' exhibits a medium to late flowering time.
15. 'Malling Ace' exhibits a medium to late fruit ripening time.
16. 'Malling Ace' exhibits a fully remontant fruit bearing habit.

The female parent of 'Malling Ace' differs from 'Malling Ace' in having flesh that is more white in color and a reflexed calyx. The male parent of 'Malling Ace' differs from 'Malling Ace' in having fruit with seeds that are even to fruit surface and a pointed conic shape. 'Malling Ace' can most closely be compared to the cultivars 'Finesse' (not patented) and 'Malling Champion' (not patented). 'Finesse' is similar to 'Malling Ace' in having fruit with an everbearing habit, an extended crop season and similar skin color. 'Finesse' differs from 'Malling Ace' in having a smaller fruit size, fruit that is conical to globose in shape, and a lower quantity of stolons. 'Malling Champion' is similar to 'Malling Ace' in having fruit with an everbearing habit, an extended crop season and similar skin color and skin glossiness. 'Malling Champion' differs from 'Malling Ace' in having fruit that are smaller size and fruit skin that is firmer.

BRIEF DESCRIPTION OF THE DRAWINGS

The accompanying color photographs illustrate the overall appearance and distinct characteristics of one-year-old plants of new cultivar as grown on table-tops in coir bags under tunnels with polyethylene covers in Faversham, Kent, United Kingdom. The photographs were taken of plants that were fruiting in early July and planted in early March from a tip taken in early July the summer before and grown as a potted plant prior to planting and overwintered above 5° C.

The photograph in FIG. 1 provides a view of the fruit of 'Malling Ace'.

Figure 1:
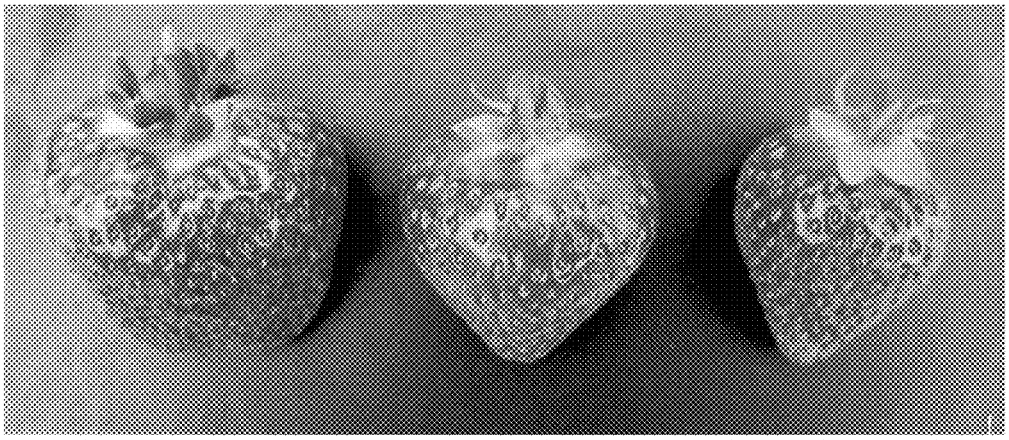
Figure 2:
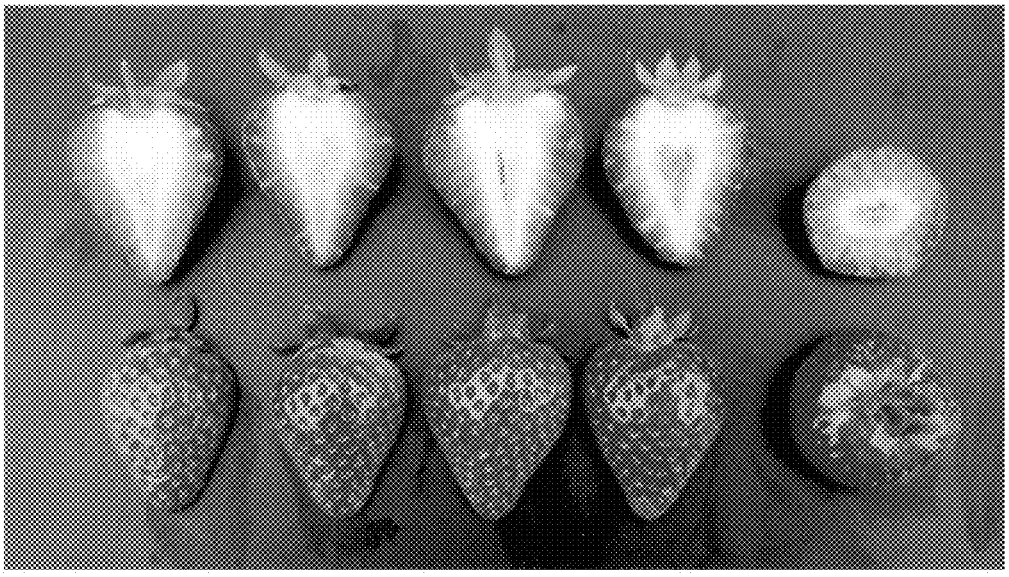

The photograph in FIG. 2 provides a view of cut fruit of 'Malling Ace'.

Figure 3:
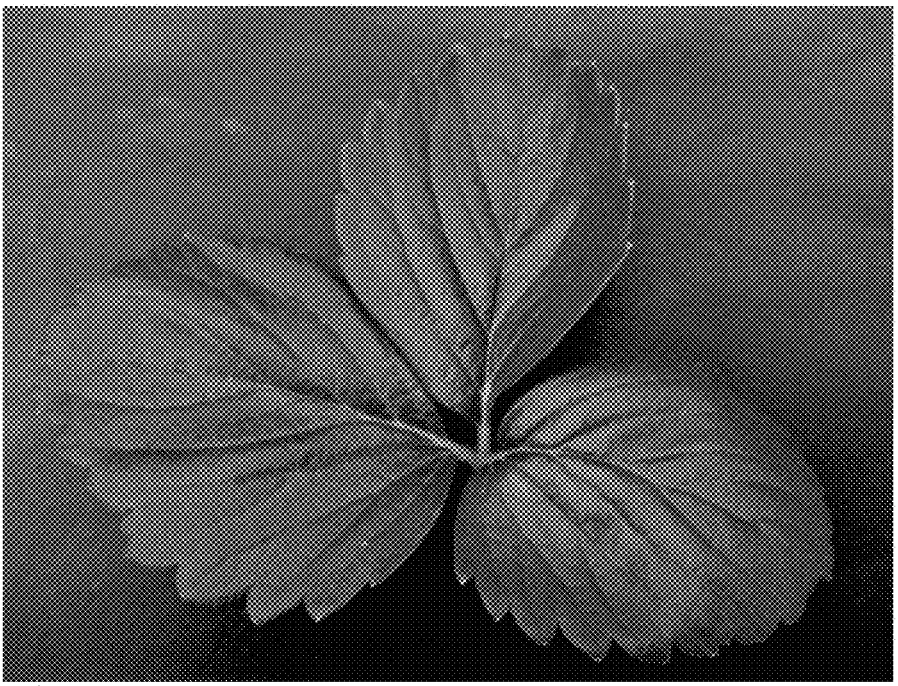

The photograph in FIG. 3 provides a view of a leaf of 'Malling Ace'.

Figure 4:
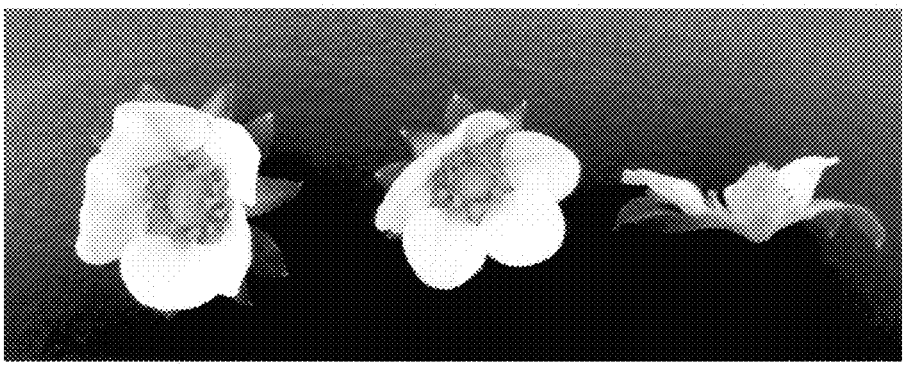

The photograph in FIG. 4 provides a close-up view of the flowers of 'Malling Ace'.

The colors in the photographs are as close as possible with digital photography techniques available, the color values cited in the detailed botanical description accurately describe the colors of the *Fragaria*.

DETAILED BOTANICAL DESCRIPTION

The following is a detailed description of one-year-old plants (Tip struck in August 2020 and fruited June 2021) of the new cultivar as grown outdoors on a protected table top culture in East Malling, Kent United Kingdom. The phenotype of the new cultivar may vary with variations in environmental, climatic, and cultural conditions, as it has not been tested under all possible environmental conditions. The color determination is in accordance with The 2001 Colour Chart of The Royal Horticultural Society, London, England, except where general color terms of ordinary dictionary significance are used.

General description:

*Blooming period.*—Starting in April and produced throughout summer in Faversham, Kent, United Kingdom.

*Plant type.*—Herbaceous fruit producing perennial.

*Plant habit.*—Semi-upright, stoloniferous.

*Height and spread.*—Reaches about 31.5 cm in width and 24.7 cm in height as a one-year-old plant.

*Cold hardiness.*—Not tested in areas where temperatures of less than 32° F. occur.

*Diseases and pests.*—Tolerance has been observed to *Phytophthora cactorum*, no susceptibility or resistance to pests has been observed.

*Root description.*—Fibrous, 155B in color.

*Root development.*—An average of 2 weeks to initiate roots and 5 weeks to produce a young rooted plant.

*Propagation.*—Rooting of stolons and tissue culture.

*Growth rate.*—Moderately vigorous.

*Stem description.*—Acaulescent.

*Stolon description.*—Average of 1 or less, An average of 28.3 cm in length and 2.79 mm in diameter, 144C, medium density of hairs with slightly outward attitude; 1.4 mm in length, N155B in color.

Foliage description:

*Leaf division.*—Compound with three leaflets.

*Leaf arrangement.*—Basal rosettes.

*Leaf shape.*—Reniform.

*Leaf color.*—Upper surface 147A, lower surface 147B.

*Leaf attachment.*—Petiolate.

*Leaf size.*—An average of 13.2 cm in length and 14.5 cm in width.

*Terminal leaflet.*—Length in relation to width is moderately longer.

*Terminal leaflet shape.*—Slightly cupped downwards at apex, convex.

*Leaflet size.*—Average of 8.2 cm in length and 7.3 cm in width.

*Terminal leaflet margins.*—Serrate to crenate.

*Terminal leaflet shape in cross section.*—Concave.

*Angle of terminal leaflet to petiole.*—34°.

*Terminal leaflet shape of base.*—Cuneate to slightly oblique.

*Terminal leaflet shape of apex.*—Subacute.

*Leaflet interveinal blistering.*—Medium.

*Leaflet venation.*—Pinnate, upper surface; 145A, lower surface; 145C.

*Leaflet surface.*—Upper surface; satiny and sparsely pubescent with soft thin hairs; 1 mm in length, matching surface color, lower surface matte with main veins and secondary veins moderately to densely covered with very thin soft adpressed hairs 1 mm in length, that match surface color.

*Leaflet color.*—Upper surface; 47A, lower surface; 147B.

*Number of leaflets.*—3.

*Number of teeth on terminal leaflet.*—Average of 19.

*Petiole.*—144C in color, average of 5 cm in length and 1.7 mm in diameter, slightly outward angle, covered with pubescent hairs 0.04 mm in length, and 144D in color.

*Petiolules.*—144D in color, oval in shape, average of 1.16 cm in length and 0.08 mm in width, covered with pubescent hairs 0.03 mm in length and N155D in color.

*Stipules anthocyanin coloration.*—Medium.

Flower description:

*Inflorescence.*—Truss.

*Inflorescence size.*—Average of 24.9 cm in length and 7.89 cm in diameter.

*Flower initiation and expression conditions.*—Temperature dependent.

*Flower longevity.*—3 to 5 days.

*Flower aspect.*—Outward to upright.

*Flower position relative to foliage.*—Upright in position relative to foliage an average of 40° to 60°.

*Flower size.*—Average 1 cm in height, 3.4 cm in diameter.

*Flower buds.*—7 mm in length to the top of the petal, 10 mm to the top of sepal, 6 mm in width, 137A in color.

*Flower number.*—4 per inflorescence.

*Flower fragrance.*—None.

*Calyx.*—Average of 2.73 cm in diameter and 3.4 mm in depth.

*Sepals.*—Lanceolate in shape, an average of 10 in number per flower with an average of 9.5 mm in length and 5.7 mm in width; sepal margin is entire, 137A in color with anthocyanin absent.

*Petals.*—Average of 5, arrangement of petals is overlapping, average of 1.25 cm in length and 1.39 cm in width, petal apex obtuse, and petal base attenuate to obtuse, margin entire, color N155D on upper surface and 155D on lower surface.

*Peduncle.*—144B in color, an average of 16.02 cm in length and 4.5 mm in diameter, held in a 75° angle facing up towards receptacle, pubescence is medium in density and 1.6 mm in length and NN155D in color.

*Pedicel.*—144C in color, an average of 5.44 cm in length and 1.8 mm in diameter, held in an upwards angle, surface is densely covered with thin soft hairs 0.9 mm in length and NN155D in color.

*Bracts.*—Average of 7, ovate in shape, 1.5 mm in length, 6.4 mm in width, color 146C, surface is moderately covered with thin soft hairs 0.9 mm in length and NN155D in color.

Reproductive organs:

*Gynoecium.*—Average of 1.5 mm in length, 0.1 mm in diameter, numerous simple, club-shaped pistils present, average of 233, color; pistils 12B, stigmas 12A, receptacle 144C.

*Androecium.*—Stamens; average of 22 per flower, anther; average of 1.5 mm in length, 0.9 mm in width, 17A in color, pollen; 17A in color and moderate in quantity.

Fruit description:

*Shape.*—Conical with some wedge shapes on primaries.

*Surface.*—Smooth with small hairs, 45A in color. Length in relation width is moderately longer.

*Calyx position.*—Variable.

*Diameter of calyx relative to fruit diameter.*—Slightly smaller.

*Adherence of calyx.*—Strong.

*Glossiness.*—Strong.

*External color (skin).*—45A.

*Internal color.*—N34B.

*Evenness of color of skin.*—Slightly uneven.

*Core of color.*—N155B.

*Fruit sweetness/taste.*—Subjective, described as subtle sweetness with moderate acidity, average Brix° 2021=8.31.

*Fruit firmness of flesh.*—Firm.

*Fruit firmness of skin.*—Medium to strong.

*Fruit weigh (secondary fruit).*—Average of 21.75 grams.

*Fruit quantity.*—Average of 36.

*Fruit size.*—3.93 cm in length and 3.52 cm in width.

*Fruit cavity.*—Absent or small/slight.

*Season of harvest.*—Everbearer, May through October with protected table-top culture, South East United Kingdom 2021 records from a March planting and de-blossoming mid-May: 1st fruit: Jun. 24, 2021, 50% pick date: Aug. 16, 2021; last pick date Sep. 23, 2021.

*Achenes.*—2A in color when mature, 0.97 mm in length and 0.78 mm in diameter, smooth and glabrous surface, average of 233 total number of seeds, position below surface.

*Longevity of fruit.*—3 to 5 days from fully ripe and held at 4° C.

*Shipping quality.*—Good, has been observed to exceed 5 days when subjected to typical supply chain conditions.

It is claimed:

1. A new and distinct cultivar of *Fragaria* plant named 'Malling Ace' as herein illustrated and described.

* * * * *